United States Patent [19]
Dirksing

[11] Patent Number: 5,863,497
[45] Date of Patent: Jan. 26, 1999

[54] ELECTROSTATIC HAND SANITIZER

[75] Inventor: Robert S. Dirksing, Cincinnati, Ohio

[73] Assignee: The Proctor & Gamble Company, Cincinnati, Ohio

[21] Appl. No.: 634,528

[22] Filed: Apr. 18, 1996

Related U.S. Application Data

[63] Continuation-in-part of Ser. No. 613,955, Mar. 11, 1996, abandoned.

[51] Int. Cl.⁶ .................................. A61L 2/18; B05B 5/25
[52] U.S. Cl. ................................ 422/28; 422/22; 422/114; 422/292; 118/629; 361/228; 601/155; 601/166; 601/169; 604/290; 134/199; 134/1
[58] Field of Search .............................. 422/22, 28, 114, 422/292; 118/629, 638; 239/3, 690, 708; 427/493; 361/228; 424/405; 601/155, 160, 166, 169; 604/19, 289, 290; 134/1, 199, 200

[56] References Cited

U.S. PATENT DOCUMENTS

| | | | |
|---|---|---|---|
| 3,127,060 | 3/1964 | Vosbikian et al. | 222/70 |
| 3,559,890 | 2/1971 | Brooks et al. | 239/304 |
| 4,066,041 | 1/1978 | Buschor et al. | 118/629 |
| 4,328,940 | 5/1982 | Malcolm | 244/136 |
| 4,356,528 | 10/1982 | Coffee | 361/226 |
| 4,381,533 | 4/1983 | Coffee | 361/228 |
| 4,467,961 | 8/1984 | Coffee | 239/1 |
| 4,476,515 | 10/1984 | Coffee | 361/226 |
| 4,549,243 | 10/1985 | Owen et al. | 361/228 |
| 4,560,107 | 12/1985 | Inculet | 239/3 |
| 4,561,037 | 12/1985 | Maclaine et al. | 361/228 |
| 4,654,190 | 3/1987 | Schlonski | 376/282 |
| 4,659,012 | 4/1987 | Coffee | 239/3 |
| 4,663,639 | 5/1987 | Owen et al. | 346/140 R |
| 4,670,010 | 6/1987 | Dragone | 604/289 |
| 4,703,891 | 11/1987 | Jackson et al. | 239/171 |
| 4,748,043 | 5/1988 | Seaver et al. | 427/30 |

(List continued on next page.)

FOREIGN PATENT DOCUMENTS

| | | |
|---|---|---|
| 0482184 A1 | 4/1992 | European Pat. Off. . |
| 0501725 A1 | 9/1992 | European Pat. Off. . |
| 0 523 961 A1 | 1/1993 | European Pat. Off. . |
| 0523963 A1 | 1/1993 | European Pat. Off. . |
| 0523964 A1 | 1/1993 | European Pat. Off. . |
| 0 567 678 A1 | 3/1993 | European Pat. Off. . |
| 0554099 A1 | 8/1993 | European Pat. Off. . |
| 0558186 A1 | 9/1993 | European Pat. Off. . |
| 0 468 735 B1 | 5/1995 | European Pat. Off. . |

(List continued on next page.)

OTHER PUBLICATIONS

Block, Seymour S., ed. Disinfection, Sterilization, and Preservation, p. 644, 1991.

*Primary Examiner*—E. Leigh McKane
*Attorney, Agent, or Firm*—Rodney M. Young; Ronald W. Kock

[57] ABSTRACT

A hand sanitizing apparatus which uses at least two electrostatic emitters to dispense germicidal fluid to substantially all the surfaces of a user's hands when both hands are placed in proximity to the electrostatic emitters. The apparatus comprises a frame on which are mounted electrostatic emitters in preferably two cells which separate spray directed at one hand from spray directed at the other hand, a reservoir of germicidal fluid in fluid communication with the electrostatic emitters, a power source adapted to supply electrostatic energy to the electrostatic emitters, and a dispensing cycle actuator which is operated by the user to distribute electrostatic energy from the power source to the electrostatic emitters so that a predetermined quantity of germicidal fluid is directed from each electrostatic emitter toward each of the user's hands during the dispensing cycle. In one embodiment each hand is sprayed with an opposite charge. In another embodiment each hand is sprayed by multiple electrostatic emitters having opposite charges. In still another embodiment the electrostatic emitter directed at each hand is pulsed such that each pulse has an opposite charge. In yet another embodiment the user is grounded so that opposite charges are unnecessary.

14 Claims, 2 Drawing Sheets

U.S. PATENT DOCUMENTS

| | | | |
|---|---|---|---|
| 4,838,456 | 6/1989 | Hamlin | 222/1 |
| 4,925,699 | 5/1990 | Fagan | 427/28 |
| 4,971,257 | 11/1990 | Birge | 239/708 |
| 5,110,616 | 5/1992 | Lair et al. | 427/9 |
| 5,135,721 | 8/1992 | Richard | 422/300 X |
| 5,193,563 | 3/1993 | Melech . | |
| 5,222,664 | 6/1993 | Noakes et al. . | |
| 5,268,166 | 12/1993 | Barnett et al. | 424/47 |
| 5,292,067 | 3/1994 | Jeffries et al. | 239/3 |
| 5,322,684 | 6/1994 | Barnett et al. | 424/47 |
| 5,366,553 | 11/1994 | Lair et al. | 118/682 |
| 5,397,028 | 3/1995 | Jesadanont | 222/1 |
| 5,490,633 | 2/1996 | Jeffries et al. | 239/691 |

FOREIGN PATENT DOCUMENTS

| | | |
|---|---|---|
| 2273673 | 6/1994 | United Kingdom . |
| 2273872 | 7/1994 | United Kingdom . |
| WO 94/11119 | 5/1994 | WIPO . |
| WO 94/12285 | 6/1994 | WIPO . |

ELECTROSTATIC HAND SANITIZER

CROSS-REFERENCE TO RELATED APPLICATION

This is a continuation-in-part of my prior application Ser. No. 08/613,955, entitled ELECTROSTATIC HAND SANITIZER, filed on Mar. 11, 1996, which is hereafter abandoned.

FIELD OF THE INVENTION

The present invention relates to hand sanitization methods and apparatus and to electrostatic spraying of fluids. Even more particularly, the present invention relates to a hand sanitization method and apparatus wherein both hands are sprayed simultaneously without a static charge buildup on the body.

BACKGROUND OF THE INVENTION

It is recognized that transmission of microbiological pathogens from the hands to other parts of the body or to food stuffs is a frequent means of communicating diseases. Some potential pathogen are E. coli, Salmonella, Shigella, Listeria, and Staph. aureus. These pathogens in contaminated food stuffs are responsible for severe illnesses and even deaths. Recent episodes involving fatalities due to contamination of food products during food handling have increased the publics' awareness of the serious potential of improper food handling. This is of special concern in fast food outlets. Although proper hand washing hygiene is generally stressed, the reality is poor compliance by the food preparers and handlers. Even when food preparers and handlers do comply with directives such as "Wash Hands before leaving Rest room", the washing practice is typically inadequate to provide sufficient sanitization of the hands. Consequently, transmission of rest room pathogens to foodstuffs is common.

Rest room contamination is not the only source. Simply shifting from raw food handling to finished food handling is a common source of contamination, for example, the common contamination of chicken with Salmonella. Furthermore, food handlers often handle money, clean tables, or mop floors, any of which can contaminate the hands and lead to transmission of disease pathogens. A trip to the rest room to wash hands between the various activities is uncommon because of the time and inconvenience involved. All to often, food handlers and preparers are not committed to proper hygiene and it is difficult for managers to enforce compliance. As pointed out previously, even washing hands does not insure sanitation if the washing practice is inadequate. Even with adequate washing, almost everyone has experience the dilemma of turning off the faucet, actuating the towel dispenser, and even opening the rest room door which provides sufficient means to recontaminate the hands. It would be a major improvement if the means for hand sanitization would be simpler and more convenient, preferably nearer the workstations. It would further be major improvement if the degree and reliability of sanitization be independent of the hand manipulation of the individual.

Some attempts have been made to remedy the problem. For example, hand sanitizing stations using germicidal gels or foams are employed. These still depend upon user hand manipulation to distribute the product. Such manipulation takes time, proper procedure and most importantly, commitment of the user. Some hand sanitizing stations require manual actuation to dispense the germicidal product. Manual contact can lead to contamination of the very implement meant to combat the problem. Foaming and gelling of the germicidal product provides a means to bulk up the product so manual distribution of the germicidal product about the hands is more likely. Unfortunately, quantities of the germicidal product beyond that required to provide sanitization are needed just to enable distribution of the product about the hands. The excess product is messy to use and requires extended evaporation time on the hands. Further, excess product may lead to other dermatological problems such as drying and cracking of the skin or even destruction of the natural micro biological flora of the hands.

European patent application publication number 0567678A1 to Mongkol on Nov. 3, 1993, discloses a fluid dispensing device for disinfecting of the hands which uses a infrared detector to activate a pressurized spray bottle when the user's hand is placed beneath a spray valve. The intent is to "spray fluids and readily irrigate in a fully automated manner the entire surfaces of the hands". However, the simple spray from a spray bottle has no affinity for the hands and thus still requires the user to move the hands beneath the spray to achieve overall coating. Furthermore, much of the active germicidal fluid is wasted as overspray, familiar to anyone who has used a paint spray can. Further still, the overspray of the germicidal fluid contaminates the air about the device and poses an inhalation problem.

U.S. Pat. No. 5,292,067 issued to Jeffries et al. on Mar. 8, 1994 discloses an apparatus for electrostatic spraying. The apparatus disclosed by Jeffries et al. is a hand held device particularly concerned with the spraying of relatively low resistivity liquids such as aqueous and alcohol based liquids used in personal care products such as deodorants, antiperspirants, scents and hair sprays. Also disclosed in U.S. Pat. No. 5,292,067 is a handgrip portion or trigger provided with a contact exposed for engagement with the hand so as to provide a path to ground in use. Since the emitted electrostatic spray carries a charge to the target skin surface, a build up of charge on the user results. Without the path to ground, the electrostatic charge of the user will accumulate usually resulting in an unpleasant static discharge.

OBJECTS OF THE INVENTION

An object of the present invention is to provide an improved hand sanitizing apparatus which provides a consistent effective hand sanitization by dispensing an even coating of germicidal fluid to the hands of the user substantially independent of the hand manipulation of the user.

Another object of the present invention is to provide a hand sanitizing apparatus which provides the minimal quantity of product required to provide effective germicidal activity on transient pathogens while minimizing the destruction to the natural flora and condition of the hands.

A further object of the present invention is to encourage compliance by providing a hand sanitizing apparatus that is simple, convenient, and fast to use with virtually no residue or inhalation effect.

Additional objects of the present invention are: to provide a hand sanitizing apparatus that sanitizes both hands simultaneously, to provide a hand sanitizing apparatus that monitors proper hand placement and treatment; and to provide a hand sanitizing apparatus that indicates visually and/or audibly the aspects of operational status, user treatment, and compliance.

SUMMARY OF THE INVENTION

In one aspect of the present invention, a hand sanitizing apparatus for applying a germicidal fluid to a user's hands comprises a frame and at least two electrostatic fluid emitters attached to the frame. It also includes a means for providing a supply of the germicidal fluid in fluid communication with the electrostatic fluid emitters and a power source adapted to supply electrostatic energy to the electrostatic fluid emitters. In addition there is a dispensing cycle actuator operated by the user to initiate distribution of electrostatic energy from the power source to the electrostatic fluid emitters so that the germicidal fluid from the fluid supply is directed to the electrostatic fluid emitters and flows therefrom toward the user's hands when the user's hands are placed in proximity to the electrostatic fluid emitters.

The frame may further comprise a first cell to apply the germicidal fluid to a right hand of the user and a second cell to simultaneously apply the germicidal fluid to a left hand of the user. Each of the first and second cells may have at least one electrostatic emitter directed at a user's hand. Where there is a first electrostatic emitter for the right hand and a second electrostatic emitter for the left hand, the first electrostatic emitter may have an electrostatic polarity opposite from the second electrostatic emitter during the dispensing cycle. Alternatively, there may be a first and a second right hand electrostatic fluid emitter attached to the frame and located to apply the germicidal fluid to a right hand and a first and a second left hand electrostatic fluid emitter attached to the frame and located to apply the germicidal fluid to a left hand, wherein the first right hand and first left hand electrostatic fluid emitters have an opposite electrostatic polarity from the second right hand and second left hand electrostatic fluid emitters during the dispensing cycle.

The apparatus may further comprise a means to dispense a predetermined quantity of the germicidal fluid onto the user's hands, such as a metering pump or a metering valve intermediate the supply of germicidal fluid and the electrostatic fluid emitter. Additionally the apparatus may further include a means for indicating the operating status of the apparatus. The supply of germicidal fluid may even be a replaceable cartridge.

In another aspect of the present invention, a method of uniformly coating a user's hands with a germicidal fluid, without the need for post-coating hand manipulation, comprises the steps of placing each of a user's hands into a hand sanitizing apparatus and initiating electrostatic spraying of each of the user's hands simultaneously with the germicidal fluid while each of the user's hands serves as a target for receiving electrostatically charged droplets of spray. The hand sanitizing apparatus has at least two electrostatic fluid emitters. Steps also include discontinuing the electrostatic spraying when sufficient germicidal fluid has been sprayed to uniformly coat each of the user's hands, such that substantially no excess fluid drips from each of the user's hands and substantially no overspray results, and removing each of the user's hands from the hand sanitizing apparatus.

The user's arms and body may provide a conductive electrical path for charges of opposite polarity between the user's hands to insure substantially no charge is built upon the user while sanitizing the user's hands. Alternatively, each of the user's hands may provide a conductive electrical path for charges of opposite polarity on each of the user's hands to insure substantially no charge is built upon the user while the user's hands. Alternatively, the electrostatic spray may be pulsed from each of the electrostatic fluid emitters, such that alternate pulses have opposite polarity, thereby insuring that substantially no charge is built upon the user while sanitizing the user's hands. Alternatively, the user may be grounded in order to insure substantially no charge is built upon the user while sanitizing the user's hands.

Furthermore, a predetermined quantity of the germicidal fluid may be dispensed onto the user's hands.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1:
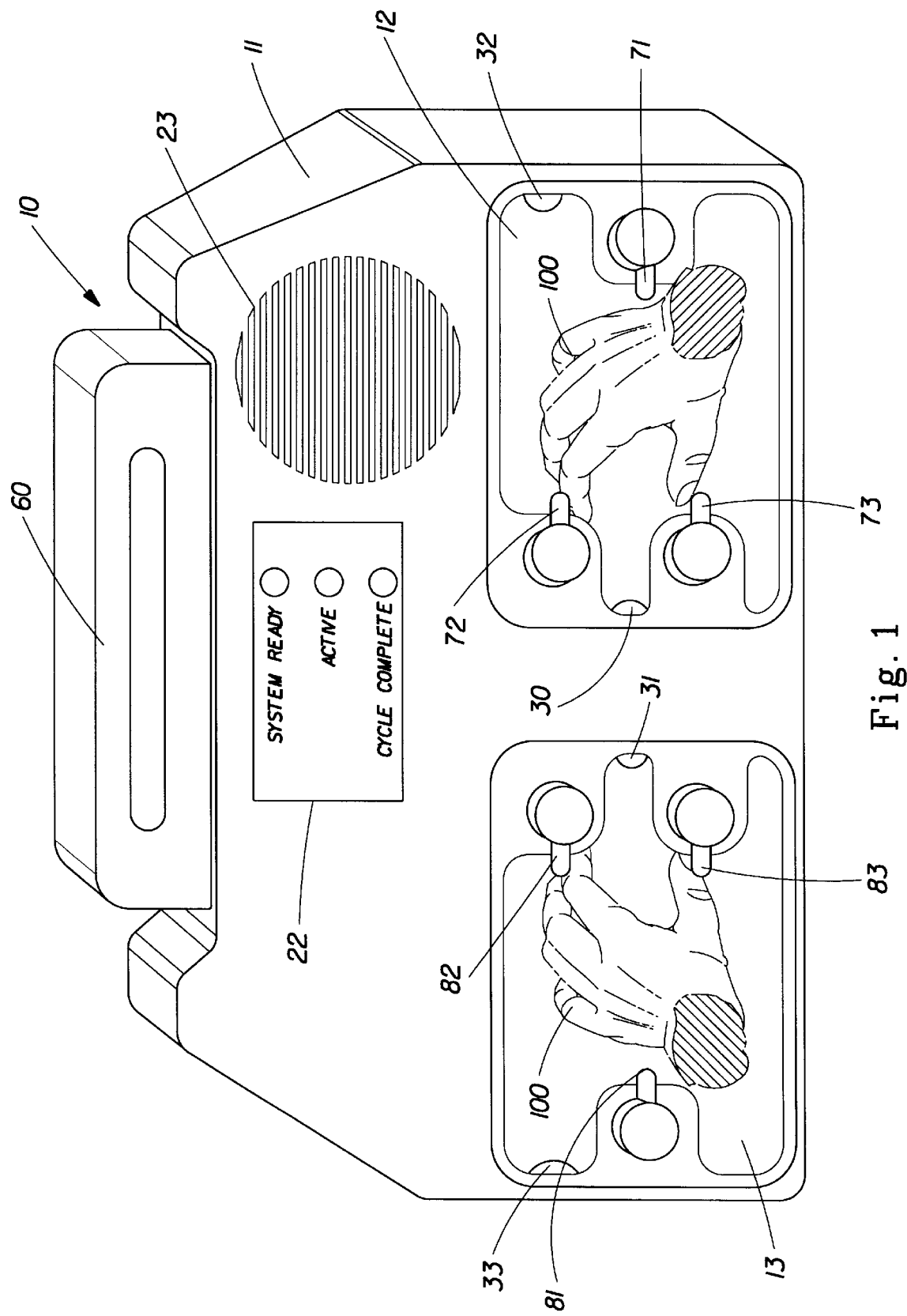
FIG. 1 is a perspective view of a preferred embodiment of hand sanitizer of the present invention.

In a preferred embodiment shown in FIG. 1, the present invention provides a hand sanitizer generally designated as 10. Hand sanitizer 10 comprises a frame 11 further comprising a right hand cell 12 and a left hand cell 13. Electrostatic spray nozzles 71, 72 and 73 are visible in right hand cell 12 while electrostatic spray nozzles 81, 82, and 83 are visible in left hand cell 13. A display panel 22 provides operational status information of the hand sanitizer and instructions to the user. An audio transducer 23 provides audible signals to compliment the visual display panel 22.

In the present invention, the term "cell" means a position where one hand is sprayed with fluid separately from the other hand. One cell for one hand is intended to be isolated from a corresponding cell for the other hand of a user so that the fluid sprays do not mix. However, cells may or may not have partitions for separation purposes if sprays are aimed such that hands may be sprayed separately without significant fluid mixing.

Figure 2:
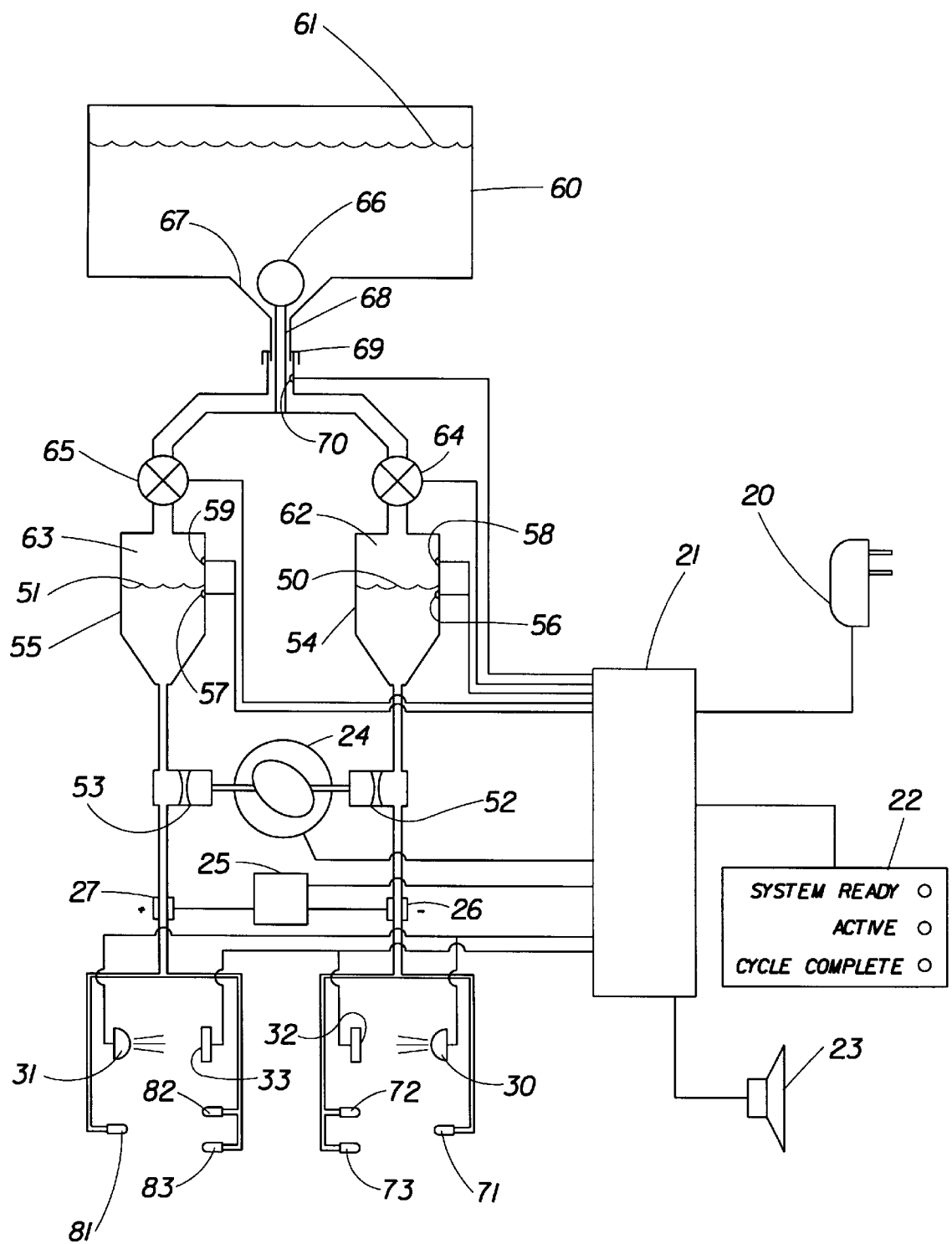
FIG. 2 is an electric and hydraulic schematic of a preferred embodiment of the present invention.

In FIG. 2, there is shown an electric and hydraulic schematic of a particularly preferred embodiment of the hand sanitizer 10. A plug-in transformer 20 reduces line voltage to an operating low voltage, preferably about 12 volts. Transformer 20 provides power to a controller 21. Controller 21 provides operational status and instruction signals to display panel 22. Controller 21 also provides appropriate signals to audio transducer 23. Controller 21 further provides power to right hand and left hand presence detection systems comprising infrared emitters 30 and 31 and infrared sensors 32 and 33. When the user of hand sanitizer 10 inserts his or her hands 100, into right and left hand cells 12 and 13, as indicated in FIG. 1, sensors 32 and 33 recognize a break in the signal from emitters 30 and 31, respectively. The infrared emitter and sensor system permits non-contact detection of the hand for the sanitization cycle. In a particularly preferred embodiment, sensors 32 and 33 comprise arrays which detect hand insertion and proper location. The sensor arrays may further detect splaying of the fingers by, for example, by "seeing" multiple shadows which indicate the finger are spread apart. For most effective hand sanitization, the fingers are preferably spread apart to enable the antimicrobial liquid to coat all the hand surfaces, even between the fingers.

Detection of the hand initiates a dispensing cycle wherein controller 21 may first indicate via display panel 22 and audio transducer that a cycle has been initiated. Alternatively, a body contact sensor could be used to initiate a dispensing cycle. However, it is most preferable that the user's hands not contact any surface while being sprayed. Concurrently with the activation of audio and visual indicators, power is distributed to high voltage generator 25 which provides high voltage of opposite polarity to electrostatic couplings 26 and 27. In FIG. 2, a negative voltage is applied to the right hand liquid germicidal product 50 and a positive voltage is applied to left hand liquid germicidal product 51. When appropriate voltage has been attained, preferably about 5000 volts to 15,000 volts, controller 21 provides power to pump motor 24 which in turn actuates pumps 52 and 53.

During a dispensing cycle, pumps 52 and 53 draw germicidal product 50 and 51 from electrical isolation reservoirs 54 and 55, respectively, and simultaneously propel germicidal product 50 and 51 through right hand electrostatic emitters 71, 72, and 73 and through left hand electrostatic emitters 81, 82, and 83, respectively. In a particularly preferred embodiment of the present invention, the electrostatic emitters are similar in operation to nozzles disclosed in U.S. Pat. No. 5,292,067 to Jeffries et al., such as the nozzles shown in FIG. 1 and FIG. 4, wherein atomization is predominantly a result of the applied high voltage electric field induced ligamentary spraying of the liquid followed by breakup of the ligament into droplets. U.S. Pat. No. 5,292,067 is hereby incorporated by reference. The opposite polarity of the high voltage applied to germicidal product 50 and 51 dispensed to the right and left hands of the user provides improvements over a single polarity electrostatic dispensing device. First, the oppositely charged germicidal sprays cancel each other through conductive paths within the user so the spray continues to be directed to a neutral target. Since a particular polarity of charge does not build up within the user, each hand is a preferential target to subsequent spray. Further, since the charges are neutralized, the user will not experience a buildup of charge and an annoying static shock when approaching an object of lower potential. Such a shock is of nuisance level, not a hazardous level, but it is nonetheless undesirable. Further still, these benefits are achieved without requiring electrostatic contact grounding of the user, thus providing enhanced sanitation by eliminating potential recontamination of the hands via manual contact ground.

Alternatively, it would be possible to ground a user other than at the hands in order to avoid the need for oppositely charged electrostatic sprays. However, such grounding is not preferred because it cannot be guaranteed effective. If a person who is not properly grounded inadvertently builds up a body charge, that person may later contact a grounded surface and experience an unpleasant and unexpected nuisance level static shock.

When a predetermined quantity of germicidal product has been dispensed to the user's hands, power from controller 21 to pumps 52 and 53 is disconnected. Power to high voltage transformer 25 is disconnected shortly thereafter to insure any residual germicidal product is emitted from the electrostatic nozzles. A signal may then be sent to the display panel 22 to inform the user that the cycle is complete and hands are sanitized. If a user prematurely withdraws his or her hands during an application cycle, sensors 32 and/or 33 will indicate to controller 21 of such condition and interrupt the dispensing cycle. In a preferred embodiment, hand sanitizer 10 will indicate to the users a premature hand removal condition either by visual or audible means and instruct the user to repeat the sanitization cycle by properly inserting the hands.

Germicidal product 50 and 51 are semi-conductive and thus may transport high voltage back to isolation reservoirs

54 and 55, respectively. In a particularly preferred embodiment of the present invention, isolation reservoirs 54 and 55 are fed from a larger common bulk reservoir 60. Since, in a particularly preferred embodiment of the present invention, germicidal products 50 and 51 are electrostatically charged to opposite polarities, germicidal products 50 and 51 must be electrically isolated from one another. It is further preferred to electrically isolate bulk germicidal supply 61 from germicidal products 50 and 51 during a dispensing cycle. In the embodiment of FIG. 2, there is shown air gaps 62 and 63 above germicidal products 50 and 51 respectively to provide such high voltage electrical isolation. Since electrostatic charging of germicidal product 50 and 51 is an intermittent operation occurring during the dispensing cycle, electrical isolation during quiescent periods between dispensing is not required. Hence, germicidal product may flow through solenoid operated valves 64 and 65 during quiescent periods. Germicidal product flow of bulk germicidal product 61 through solenoid operated valves 64 and 65 onto the surfaces of germicidal products 50 and 51 in isolation reservoirs 54 and 55, respectively, during a dispensing cycle could result in an electrical path for high voltage transmission to bulk germicidal product 61 or between germicidal products 50 and 51. Low level sensors 56 and 57 detect low level in isolation reservoirs 54 and 55 in order that controller 21 can activate solenoid operated valves 64 and 65 between dispensing cycles. High level sensors 58 and 59 detect high levels of germicidal products 50 and 51, respectively, to indicate to controller 21 to deactivate solenoid operated valves 64 and 65, respectively. Other means for providing high voltage isolation may be used. For example, a high voltage peristaltic isolation pump wherein rollers pinch off a resilient tube in multiple locations about a cylindrical chamber may be employed to provide electrical isolation and may further serve as a pumping means. Sensor 70 detects low germicidal fluid level of bulk reservoir 60 and may be used by controller 21 to provide an appropriate indication to the users.

In a particularly preferred embodiment of the present invention, bulk reservoir 60 is a replaceable cartridge prefilled with a quantity of germicidal product. A typical dispensing cycle may apply about 0.3 ml to about 0.5 ml of germicidal product. A bulk reservoir 60 having a capacity of about one liter and which may be housed within the frame of the hand sanitizer could provide 2000 dispensing cycles. Larger bulk supplies may be remote from the actual hand sanitizer and possibly connected by means of a small tube. The predetermined quantity dispensed would depend upon several factors, e.g., the particular germicidal ingredients, size of user's hands and the degree of germ kill required. Two chemicals which have been shown to provide excellent germicidal effects are aqueous solutions of ethyl alcohol and isopropyl alcohol. A particular advantage of the hand sanitizer of the present invention is the ability to apply a light even coating of the germicidal product to the hand surfaces because of the electrostatic attraction of the germicidal product to the user's hands. The light coating minimizes the adverse affects of the germicidal products such as dehydration of the skin, and destruction of the natural flora of the hands.

Referring to FIG. 2, bulk reservoir 60 may be removed from snap seal 69 upon emptying of bulk germicidal product 61. Upon removal of bulk reservoir 60, probe 68 will be withdrawn from the interior of bulk reservoir 60 permitting check ball 66 to seat onto seal surface 67 thus trapping any residual germicidal product 61. Upon installation of a subsequent bulk reservoir 60 in, for example, the form of a prefilled cartridge, probe 68 will dislodge check ball 66 from seal surface 67 thus permitting flow of bulk germicidal product 61 to solenoid operated valves 64 and 65. Other means may be employed to open a new prefilled product cartridge upon installation such as pierced membranes and deformable resilient valves.

In an alternative embodiment of the hand sanitizer of the present invention, a first electrostatic emitter in a right hand cell is charged to high voltage positive electrostatic polarity while a second electrostatic emitter in the right hand cell is charged to a high voltage negative electrostatic polarity during a dispensing cycle. A similar configuration would be presented in a left hand cell, i.e., opposite electrostatic polarities between electrostatic emitters in the left hand cell. The opposite charges carried by the emitted electrostatic sprays from the oppositely charged electrostatic emitters within each cell tend to cancel upon contact with the hands through natural conductive paths within the hand. The effect is generally similar to the neutralization of opposite charges between the right and left hands in hand sanitizers having opposite charges between right and left hand cells. However, an advantage of the opposite electrostatic charged sprays within each cell is that an individual hand may be treated without the buildup of electrostatic within the user.

In a second alternative embodiment, the electrostatic emitters are pulsed on and off. Each pulse has an opposite charge. This is another way to prevent a charge buildup on a non-grounded user and to thereby maintain the user's hands as neutrally charged targets during electrostatic spraying.

In hand sanitizers of the present invention, having more than one electrostatic emitter in each of the right and left hand cells, and wherein the electrostatic polarity of the electrostatic emitters of the right hand cell is opposite of the electrostatic polarity of the electrostatic emitters of the left hand cell, the similar electrostatic polarity the charged emitted sprays cause them to be repel each other. The result is a more diffuse spray versus opposite electrostatic polarity within each cell. The hand, however, still remains essentially electrically neutral and thus still is the preferred target for the emitted sprays.

While particular embodiments of the present invention have been illustrated and described, it will be obvious to those skilled in the art that various changes and modifications may be made without departing from the spirit and scope of the invention, and it is intended to cover in the appended claims all such modification that are within the scope of the invention.

What is claimed is:

1. A hand sanitizing apparatus for applying a germicidal fluid to a user's hands comprising:

a) a frame having a first cell to apply a germicidal fluid to a right hand of a user and a second cell to simultaneously apply said germicidal fluid to a left hand of the user, such that said germicidal fluid from said first cell does not mix with said germicidal fluid from said second cell;

b) a first and a second electrostatic fluid emitter attached to said frame, said first electrostatic fluid emitter having an opposite electrostatic polarity from said second electrostatic fluid emitter during a dispensing cycle wherein said first electrostatic fluid emitter is located at said first cell and said second electrostatic fluid emitter is located at said second cell;

c) means for providing a supply of said germicidal fluid in fluid communication with said first and second electrostatic fluid emitters;

d) a power source adapted to supply electrostatic energy to said first and second electrostatic fluid emitters; and e) a dispensing cycle actuator operated by the user to initiate distribution of electrostatic energy from said power source and a predetermined quantity of said germicidal fluid from said supply to said first and second electrostatic fluid emitters so that said germicidal fluid from said supply is directed to said first and second electrostatic fluid emitters, said germicidal fluid flowing as an electrostatic spray from said first and second electrostatic fluid emitters toward the user's right and left hands respectively when the user's right and left hands are placed in proximity to said first and second electrostatic fluid emitters respectively.

2. The apparatus of claim 1, further comprising a means for indicating operating status of said apparatus.

3. The apparatus of claim 1, wherein said supply of germicidal fluid comprises a replaceable cartridge.

4. The apparatus of claim 1 wherein said germicidal fluid is selected from the group consisting of an aqueous solution of ethyl alcohol and an aqueous solution of isopropyl alcohol.

5. The hand sanitizing apparatus of claim 1 wherein each of the user's hands provides a conductive electrical path for charges of opposite polarity directed to each of the user's hands to insure substantially no charge is built upon the user while sanitizing the user's hands.

6. The hand sanitizing apparatus of claim 1 wherein said electrostatic spray is pulsed from each of said at least two electrostatic fluid emitters, such that alternate pulses have opposite polarity, thereby insuring that substantially no charge is built upon the user while sanitizing the user's hands.

7. A hand sanitizing apparatus for applying a germicidal fluid to a user's hands comprising:

a) a frame having a first cell separated from a second cell;

b) a first electrostatic fluid emitter attached to said frame and located to apply said germicidal fluid to a right hand of the user in said first cell;

c) a second electrostatic fluid emitter attached to said frame and located to simultaneously apply said germicidal fluid to a left hand of the user in said second cell, said first electrostatic fluid emitter having an opposite electrostatic polarity from said second electrostatic fluid emitter during said dispensing cycle and said germicidal fluid from said first cell does not mix with said germicidal fluid from said second cell;

d) means for providing a supply of said germicidal fluid in fluid communication with said first and second electrostatic fluid emitter;

e) a power source adapted to supply electrostatic energy to said first and second electrostatic fluid emitters;

i) a non-contact dispensing cycle actuator operated by the user to initiate distribution of electrostatic energy from said power source and a predetermined quantity of said germicidal fluid from said supply to said first and second electrostatic fluid emitters so that said germicidal fluid from said supply is directed to said first and second electrostatic fluid emitters and flows from said first and second electrostatic fluid emitters toward the user's hands when the user's hands are placed in proximity to said first and second electrostatic fluid emitters and wherein each of the user's hands provides a conductive electrical path for charges of opposite polarity directed to each of the user's hands to insure substantially no charge is built upon the user while sanitizing the user's hands.

8. The apparatus of claim 7, wherein each of said first and second electrostatic fluid emitters has a plurality of electrostatic nozzles aimed at all sides of a user's hand.

9. The apparatus of claim 7, further comprising a means for indicating operating status of said hand sanitizing apparatus.

10. The apparatus of claim 7, wherein said supply of germicidal fluid comprises a replaceable cartridge.

11. The apparatus of claim 7 wherein said germicidal fluid is selected from the group consisting of an aqueous solution of ethyl alcohol and an aqueous solution of isopropyl alcohol.

12. The hand sanitizing apparatus of claim 7 wherein said electrostatic spray is pulsed from each of said at least two electrostatic fluid emitters, such that alternate pulses have opposite polarity.

13. A method of uniformly coating a user's hands with a germicidal fluid, without the need for post-coating hand manipulation, said method comprising the steps of:

a) placing each of a user's hands into a hand sanitizing apparatus, said hand sanitizing apparatus having a first and a second electrostatic fluid emitter wherein said first electrostatic fluid emitter is located at a first cell and said second electrostatic fluid emitter is located at a second cell, said first electrostatic fluid emitter having an opposite electrostatic polarity from said second electrostatic fluid emitter during electrostatic spraying;

b) initiating electrostatic spraying of each of the user's hands simultaneously with said germicidal fluid while each of the user's hands serves as a target of lower electrostatic potential for receiving droplets of spray of higher electrostatic potential wherein each of the user's hands provides a conductive electrical path for charges of opposite polarity directed to each of the user's hands to insure substantially no charge is built upon the user while sanitizing the user's hands and said germicidal fluid from said first cell does not mix with said germicidal fluid from said second cell;

c) discontinuing said electrostatic spraying when sufficient germicidal fluid has been sprayed to uniformly coat each of the user's hands such that substantially no excess fluid drips from each of the user's hands and substantially no overspray results; and d) removing each of the user's hands from said hand sanitizing apparatus.

14. The method of claim 13 wherein said germicidal fluid is selected from the group consisting of an aqueous solution of ethyl alcohol and an aqueous solution of isopropyl alcohol.

* * * * *